US012339281B2

(12) United States Patent
Ohara et al.

(10) Patent No.: US 12,339,281 B2
(45) Date of Patent: Jun. 24, 2025

(54) IMMUNOCHROMATOGRAPHIC KIT AND METHOD FOR DETECTING MYCOBACTERIUM TUBERCULOSIS

(71) Applicant: FUJIFILM Corporation, Tokyo (JP)

(72) Inventors: Tomoya Ohara, Ashigarakami-gun (JP); Natsuki Oyabu, Ashigarakami-gun (JP); Atsuhiko Wada, Ashigarakami-gun (JP); Junichi Katada, Ashigarakami-gun (JP); Dai Ujihara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/156,214

(22) Filed: Jan. 18, 2023

(65) Prior Publication Data

US 2023/0273204 A1 Aug. 31, 2023

Related U.S. Application Data

(60) Division of application No. 17/187,264, filed on Feb. 26, 2021, now abandoned, which is a continuation of application No. PCT/JP2019/034112, filed on Aug. 30, 2019.

(30) Foreign Application Priority Data

Aug. 31, 2018 (JP) ................. 2018-163097

(51) Int. Cl.
| G01N 33/569 | (2006.01) |
| C07K 16/12 | (2006.01) |
| G01N 33/543 | (2006.01) |
| G01N 33/549 | (2006.01) |

(52) U.S. Cl.
CPC ..... *G01N 33/5695* (2013.01); *C07K 16/1289* (2013.01); *G01N 33/54388* (2021.08); *G01N 33/549* (2013.01); *G01N 2333/35* (2013.01); *G01N 2400/00* (2013.01); *G01N 2469/10* (2013.01)

(58) Field of Classification Search
None
See application file for complete search history.

(56) References Cited

U.S. PATENT DOCUMENTS

| 2006/0127406 A1 | 6/2006 | Koulchin et al. |
| 2013/0084580 A1 | 4/2013 | Wada et al. |
| 2013/0309237 A1 | 11/2013 | Macary et al. |
| 2014/0377770 A1 | 12/2014 | Bischof et al. |
| 2016/0083458 A1 | 3/2016 | Katsuragi et al. |
| 2017/0307603 A1 | 10/2017 | Wada |
| 2017/0315116 A1 | 11/2017 | Shimada et al. |
| 2018/0128827 A1 | 5/2018 | Bischof et al. |
| 2018/0292398 A1 | 10/2018 | Wada et al. |

FOREIGN PATENT DOCUMENTS

| CN | 101470114 A | 7/2009 |
| CN | 103033610 A | 4/2013 |
| CN | 104144944 A | 11/2014 |
| CN | 107110858 A | 8/2017 |
| CN | 107407676 A | 11/2017 |
| CN | 108369228 A | 8/2018 |
| EP | 2 821 415 A1 | 1/2015 |
| EP | 3 225 995 A1 | 10/2017 |
| JP | 2008-507544 A | 3/2008 |
| JP | 2013-213803 A | 10/2013 |
| JP | 2015-509201 A | 3/2015 |
| JP | 2016-99283 A | 5/2016 |
| WO | WO 2008/071335 A1 | 6/2008 |
| WO | WO 2012/102679 A1 | 8/2012 |
| WO | WO 2013/129634 A1 | 9/2013 |
| WO | WO 2017/104143 A1 | 6/2017 |
| WO | WO 2017/139153 A1 | 8/2017 |
| WO | WO 2020018806 A1 * | 1/2020 |

OTHER PUBLICATIONS

Cashmore et al. J. Biol. Chem. 292: 4976-4986, 2017, Abstract.*
Broger et al. Lancet Infect. Dis. 19: 852-861, Published online May 30, 2019.*
Chinese Office Action for corresponding Chinese Application No. 201980056681.4, dated Feb. 23, 2024, with English translation.
Chinese Office Action and Search Report for corresponding Chinese Application No. 201980056681.4, dated Aug. 23, 2023, with an English translation.
Choudhary et al., "Characterization of the Antigenic Heterogeneity of Lipoarabinomannan, the Major Surface Glycolipid of Mycobacterium tuberculosis, and Complexity of Antibody Specificities toward This Antigen," The Journal of Immunology, vol. 200, No. 9, May 1, 2018, pp. 3053-3066.
Extended European Search Report for corresponding European Application No. 19855891.8, dated Oct. 25, 2021.
Final Office Action issued in U.S. Appl. No. 17/187,264, mailed on Oct. 19, 2022.
International Preliminary Report on Patentability and Written Opinion of the International Searching Authority (Forms PCT/IB/326, PCT/IB/373 and PCT/ISA/237) for corresponding International Application No. PCT/JP2019/034112, dated Mar. 11, 2021, with English translation.

(Continued)

*Primary Examiner* — S. Devi

(74) *Attorney, Agent, or Firm* — Birch, Stewart, Kolasch & Birch, LLP

(57) ABSTRACT

An object of the present invention is to provide an immunochromatographic kit and a method, which are capable of detecting *Mycobacterium tuberculosis* with high-sensitivity and specificity. According to the present invention, an immunochromatographic kit for detecting *Mycobacterium tuberculosis* is provided, the kit including: a label substance modified with a first antibody against lipoarabinomannan; a porous carrier having a reaction site holding a second antibody against lipoarabinomannan; a compound containing silver; and a reducing agent reducing silver ions, in which at least one of the first antibody or the second antibody is a monoclonal antibody.

14 Claims, 3 Drawing Sheets

Specification includes a Sequence Listing.

(56) References Cited

OTHER PUBLICATIONS

International Search Report (Form PCT/ISA/210) for corresponding International Application No. PCT/JP2019/034112, dated Nov. 26, 2019, with English translation.
Japanese Office Action for corresponding Japanese Application No. 2020-539625, dated Apr. 12, 2022, with English translation.
Japanese Office Action for corresponding Japanese Application No. 2020-539625, dated Oct. 12, 2021, with English translation.
Lawn, "Point-of-care detection of lipoarabinomannan (LAM) in urine for diagnosis of HIV-associated tuberculosis: a state of the art review," BMC Infectious Diseases, vol. 12, No. 103, Apr. 26, 2012, pp. 1-12.
Non-Final Office Action issued in U.S. Appl. No. 17/187,264, mailed on Jun. 16, 2022.
Restriction/Election Requirement issued in US Application No. 17/187.264, mailed on Dec. 13, 2021.
European Communication pursuant to Article 94(3) EPC for corresponding European Application No. 19855891.8, dated Nov. 15, 2024.
Chinese Office Action for corresponding Chinese Application No. 201980056681.4, dated Jul. 6, 2024, with an English translation.
European Communication pursuant to Article 94(3) EPC for corresponding European Application No. 19 855 891.8, dated Mar. 27, 2025.

* cited by examiner

IMMUNOCHROMATOGRAPHIC KIT AND METHOD FOR DETECTING MYCOBACTERIUM TUBERCULOSIS

CROSS-REFERENCE TO RELATED APPLICATIONS

This application is a Divisional of U.S. application Ser. No. 17/187,264 filed on Feb. 26, 2021, now abandoned, which is a Continuation of PCT International Application No. PCT/JP2019/034112 filed on Aug. 30, 2019, which claims priority under 35 U.S.C. § 119 (a) to Japanese Patent Application No. 2018-163097 filed on Aug. 31, 2018. Each of the above applications are hereby expressly incorporated by reference, in its entirety, into the present application.

REFERENCE TO SEQUENCE LISTING SUBMITTED VIA EFS-WEB

This application includes an electronically submitted sequence listing in .XML format. The .XML file contains a sequence listing entitled "2870-0780PUS2_Substitute_Sequence_Listing.xml" created on Apr. 8, 2023 and is 18,714 bytes in size. The sequence listing contained in this .XML file is part of the specification and is hereby incorporated by reference herein in its entirety.

BACKGROUND OF THE INVENTION

1. Field of the Invention

The present invention relates to an immunochromatographic kit for detecting *Mycobacterium tuberculosis*, the kit including a label substance, a porous carrier, a compound containing silver, and a reducing agent capable of reducing silver ions. The present invention further relates to a method for detecting *Mycobacterium tuberculosis* using a label substance, a porous carrier, a compound containing silver, and a reducing agent capable of reducing silver ions.

2. Description of the Related Art

Among immunoassay methods, an immunochromatographic method is generally utilized, because operation is easy and measurement can be performed within a short period of time. Competitive responses or sandwich-based responses are widely used as an immune response used in the immunochromatographic method. Among them, sandwich-based responses are the mainstream in the immunochromatographic method, and in a typical example thereof, the following operation is performed in order to detect a test substance composed of antigens in a specimen. First, fine particles sensitized with an antibody against an antigen which is a test substance are immobilized as solid-phase fine particles on a chromatographic carrier, or an antibody itself is directly immobilized on a chromatographic carrier, and thereby a chromatographic carrier having a reaction site is prepared. Meanwhile, labeled fine particles are sensitized with an antibody against a test substance to prepare sensitized labeled fine particles. The sensitized labeled fine particles are then chromatographically moved together with a specimen on a chromatographic carrier. By the above operation, the immobilized antibody serves as an immobilization reagent at a reaction site formed on the chromatographic carrier, and the sensitized labeled fine particles specifically bind to this immobilized antibody via an antigen which is a test substance. As a result, by visually determining the presence or absence or a degree of signals generated by the sensitized labeled fine particles trapped at the reaction site, it is possible to measure the presence or absence or an amount of a test substance in a specimen.

In the immunochromatographic method, detection signals may be amplified in some cases in order to avoid a problem of false negatives indicating that an antigen is not detected due to a low sensitivity. As a method of signal amplification, there are known method such as a method in which an enzyme such as alkaline phosphatase or peroxidase is used as a label, and a method of amplification (silver amplification) in which a compound containing silver and a reducing agent capable of reducing silver ions are used for a label selected from the group consisting of a metal colloid label and a metal sulfide label.

Major tuberculosis antigens are glycolipids, which are major constituents of cell membranes and cell walls. Among glycolipids, it is known that lipoarabinomannan (LAM) is detected for diagnosis of tuberculosis, which is an infectious disease. For example, WO2013/129634A discloses an immunoassay for mycobacterial diseases by using a monoclonal antibody that specifically binds to lipoarabinomannan, and the above antibody. WO2017/139153A discloses an immunoassay using a monoclonal antibody that specifically binds to lipoarabinomannan. JP2008-507544A discloses a method and a kit which are for detecting *Mycobacterium tuberculosis* by using a polyclonal antibody that specifically binds to lipoarabinomannan. WO2012/102679A discloses a method and a kit which are for detecting *Mycobacterium tuberculosis* by using a monoclonal antibody that specifically binds to lipoarabinomannan. BMC Infectious Diseases 2012, 12: 103 discloses detection of lipoarabinomannan by using a monoclonal antibody that recognizes an epitope having a 5-deoxy-5-methylthio-xylofuranose structure (also referred to as an MTX structure) of lipoarabinomannan. J Immunol. 2018 May 1; 200(9): 3053-3066 discloses a method and a kit which are for detecting *Mycobacterium tuberculosis* by using a polyclonal antibody that specifically binds to lipoarabinomannan.

SUMMARY OF THE INVENTION

Lack of diagnostic sensitivity, lack of specificity for *Mycobacterium tuberculosis* caused by cross-reaction with a nontuberculous mycobacterial group due to use of polyclonal antibodies, and the like have been pointed out in existing kits and methods for detecting lipoarabinomannan (LAM) and diagnosing tuberculosis, which is an infectious disease. Because lack of diagnostic sensitivity leads to delayed treatment of tuberculosis, and lack of specificity leads to incorrect treatment for a nontuberculous mycobacterial group that is resistant to antituberculous drugs, kits and methods for detecting LAM with high-sensitivity and specificity are desired.

An object of the present invention is to provide an immunochromatographic kit and a method, which are capable of detecting *Mycobacterium tuberculosis* with high-sensitivity and specificity.

As a result of intensive studies to achieve the above-mentioned object, the inventors of the present invention have found that it is possible to detect *Mycobacterium tuberculosis* with high-sensitivity and specificity by incorporating a compound containing silver, and a reducing agent capable of reducing silver ions, and by allowing at least one of a first antibody or a second antibody to be a monoclonal antibody, in an immunochromatographic kit for detecting *Mycobacterium tuberculosis*, the kit including a label substance modified with the first antibody against lipoarabinomannan, and a porous carrier having a reaction site holding the second antibody against lipoarabinomannan. Therefore, the inventors of the present invention have completed the present invention.

That is, according to the present invention, the following inventions are provided.

[1] An immunochromatographic kit for detecting *Mycobacterium tuberculosis*, the kit comprising:
  a label substance modified with a first antibody against lipoarabinomannan;
  a porous carrier having a reaction site holding a second antibody against lipoarabinomannan;
  a compound containing silver; and
  a reducing agent reducing silver ions,
  in which at least one of the first antibody or the second antibody is a monoclonal antibody.

[2] The immunochromatographic kit according to [1], in which at least one of the first antibody or the second antibody is a monoclonal antibody that recognizes a 5-deoxy-5-methylthio-xylofuranose structure of lipoarabinomannan.

[3] The immunochromatographic kit according to [1] or [2], in which both of the first antibody and the second antibody are monoclonal antibodies.

[4] The immunochromatographic kit according to any one of [1] to [3], in which the label substance is a metal particle.

[5] The immunochromatographic kit according to any one of [1] to [4], in which the label substance is gold, silver, platinum, or a compound thereof.

[6] The immunochromatographic kit according to any one of [1] to [5], in which an average particle size of the label substance 1 nm to 500 nm.

[7] The immunochromatographic kit according to any one of [1] to [6], in which the compound containing silver is silver nitrate.

[8] The immunochromatographic kit according to any one of [1] to [7], in which the reducing agent reducing silver ions is $Fe^{2+}$.

[9] The immunochromatographic kit according to any one of [1] to [8], in which the porous carrier is a nitrocellulose carrier.

[10] The immunochromatographic kit according to any one of [1] to [9], further comprising a coloring reagent for detecting the reducing agent reducing silver ions.

[11] The immunochromatographic kit according to [10], in which the coloring reagent is a compound that reacts with ions and develops color.

[12] The immunochromatographic kit according to [10] or [11], in which the coloring reagent is a compound that reacts with $Fe^{2+}$ ions and develops color.

[13] The immunochromatographic kit according to any one of [10] to [121], in which the coloring reagent is a compound having a phenanthroline skeleton.

[14] The immunochromatographic kit according to [10] or [11], in which the coloring reagent is a compound that reacts with $H^+$ ions and develops color.

[15] The immunochromatographic kit according to any one of [10] to [14], in which the coloring reagent is carried by the porous carrier.

[16] The immunochromatographic kit according to any one of [10] to [15], in which the coloring reagent does not substantially move in the porous carrier in a case where any of an aqueous solution containing a test specimen or an aqueous solution containing the reducing agent reducing silver ions is spread.

[17] The immunochromatographic kit according to any one of [1] to [16], further comprising a housing case including the porous carrier having the reaction site, the compound containing silver, and the reducing agent reducing silver ions.

[18] The immunochromatographic kit according to any one of [1] to [17], further comprising: pots each including a tearable member, in which the compound containing silver and the reducing agent reducing silver ions are respectively sealed in the pots.

[19] The immunochromatographic kit according to [18], in which the pots are broken by an external force.

[20] A method for detecting *Mycobacterium tuberculosis*, the method comprising:
  a step of spreading a complex body of lipoarabinomannan in a specimen and a label substance modified with a first antibody against lipoarabinomannan on a porous carrier having a reaction site holding a second antibody against lipoarabinomannan;
  a step of trapping the complex body at the reaction site; and
  a step of amplifying the label substance of the complex body trapped at the reaction site using a compound containing silver and a reducing agent reducing silver ions,
  in which at least one of the first antibody or the second antibody is a monoclonal antibody.

[21] The method for detecting *Mycobacterium tuberculosis* according to [20], in which at least one of the first antibody or the second antibody is a monoclonal antibody that recognizes a 5-deoxy-5-methylthio-xylofuranose structure of lipoarabinomannan.

[22] The method for detecting *Mycobacterium tuberculosis* according to [20] or [21], the method further comprising detecting a label substance having an average particle size of equal to or more than 1 μm and equal to or less than 20 μm in a case of detection.

According to an immunochromatographic kit and a method according to the aspects of the present invention, *Mycobacterium tuberculosis* can be detected with high-sensitivity and specificity.

DESCRIPTION OF THE PREFERRED EMBODIMENTS

Figure 1:
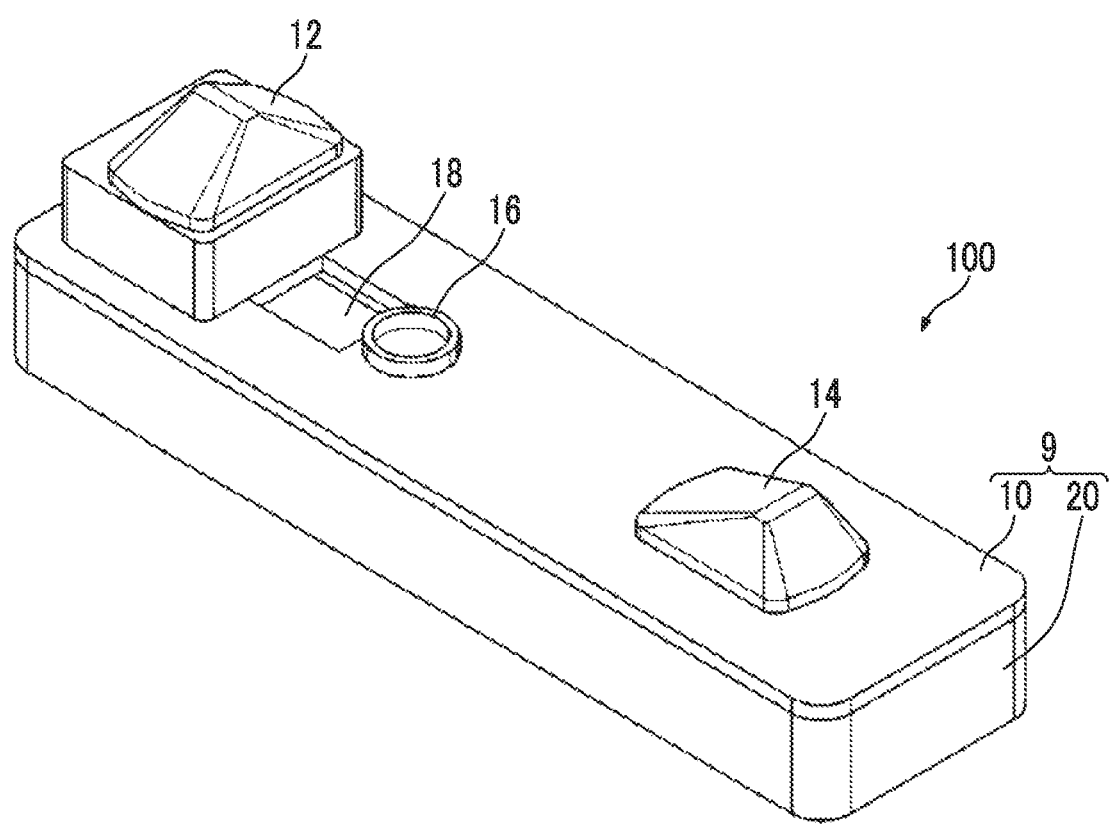
FIG. 1 is a perspective view showing an example of an immunochromatographic kit.

Hereinafter, embodiments of the present invention will be described in detail.

Numerical value ranges expressed using "to" in the present specification mean a range including numerical values described before and after "to" as a minimum value and a maximum value.

An immunochromatographic kit for detecting *Mycobacterium tuberculosis* according to the embodiment of the present invention is kit including.
  a label substance modified with a first antibody against lipoarabinomannan;

a porous carrier having a reaction site holding a second antibody against lipoarabinomannan;

a compound containing silver; and a reducing agent capable of reducing silver ions, in which at least one of the first antibody or the second antibody is a monoclonal antibody.

A method for detecting *Mycobacterium tuberculosis* according to the embodiment of the present invention is a method including:

a step of spreading a complex body of lipoarabinomannan in a specimen and a label substance modified with a first antibody against lipoarabinomannan on a porous carrier having a reaction site holding a second antibody against lipoarabinomannan;

a step of trapping the complex body at the reaction site; and a step of amplifying the label substance of the complex body trapped at the reaction site using a compound containing silver and a reducing agent reducing silver ions, in which at least one of the first antibody or the second antibody is a monoclonal antibody.

According to the immunochromatographic kit and the method for detecting *Mycobacterium tuberculosis* of the embodiment of the present invention, it is possible to perform qualitative analysis or quantitative analysis of *Mycobacterium tuberculosis*, and thereby it is possible to perform diagnosis of tuberculosis.

Examples of combinations of the first antibody and the second antibody include:

a case in which the first antibody is a monoclonal antibody and the second antibody is a polyclonal antibody;

a case in which the first antibody is a polyclonal antibody and the second antibody is a monoclonal antibody; and a case in which the first antibody is a monoclonal antibody and the second antibody is a monoclonal antibody. Among the examples, the case in which the first antibody is a monoclonal antibody and the second antibody is a monoclonal antibody is preferable.

The first antibody against lipoarabinomannan and the second antibody against lipoarabinomannan are not particularly limited. For example, it is possible to use antisera prepared from animal sera immunized with lipoarabinomannan, immunoglobulin fractions purified from antiserum, monoclonal antibodies obtained by cell fusion using animal spleen cells immunized with lipoarabinomannan, or fragments thereof [for example, F(ab')$_2$, Fab, Fab', or Fv], or single-stranded antibodies (such as scFv). Preparation of these antibodies can be performed by a conventional method.

It is preferable that at least one of the first antibody against lipoarabinomannan or the second antibody against lipoarabinomannan be a monoclonal antibody that recognizes a 5-deoxy-5-methylthio-xylofuranose structure (also referred to as an MTX structure) of lipoarabinomannan.

It is possible to use an A194-01 antibody disclosed in WO2017/139153A as an example of the first antibody against lipoarabinomannan. All contents disclosed in WO2017/139153A relating to the A194-01 antibody are incorporated in the present specification as a part of the disclosure of the present specification.

Amino acid sequences of a complementarity-determining region (CDR) of the A194-01 antibody are described below.

```
Light chain CDR1:
                                        (SEQ ID NO: 1)
RSIRSA Light chain CDR2:
                                        (SEQ ID NO: 2)
GAS Light chain CDR3:
                                        (SEQ ID NO: 3)
QQYDFWYTF Heavy chain CDR1:
                                        (SEQ ID NO: 4)
GFNFEDFG Heavy chain CDR2:
                                        (SEQ ID NO: 5)
ISWNGANI Heavy chain CDR3:
                                        (SEQ ID NO: 6)
IDWYRDDYYKMDV
```

Base sequences and amino acid sequences of the heavy chains and light chains of the A194-01 antibody are shown below.

Base sequence of heavy chain (SEQ ID NO: 7)
Amino acid sequence of heavy chain (SEQ ID NO: 8)
Base sequence of light chain (kappa) (SEQ ID NO: 9)
Amino acid sequence of light chain (kappa) (SEQ ID NO: 10)

Examples of the second antibody against lipoarabinomannan include an antibody having a sequence described as MoAb1 in paragraph [0080] of WO2013/129634A (hereinafter referred to as MoAb1 antibody). All contents disclosed in WO2013/129634A relating to the MoAb1 antibody are incorporated in the present specification as a part of the disclosure of the present specification. According to J Immunol. 2018 May 1; 200(9): 3053-3066, the MoAb1 antibody is a monoclonal antibody that recognizes an epitope having a 5-deoxy-5-methylthio-xylofuranose structure (also referred to as an MTX structure) of lipoarabinomannan.

Examples of the MoAb1 antibody include an antibody having a structure in which a heavy chain variable region containing heavy chains CDR1 to CDR3 of the following (a) to (c), and a light chain variable region containing light chains CDR1 to CDR3 of the following (d) to (f) are joined via a linker.

(a) Heavy chain CDR1 consisting of an amino acid sequence set forth in SEQ ID NO: 11
(b) Heavy chain CDR2 consisting of an amino acid sequence set forth in SEQ ID NO: 12
(c) Heavy chain CDR3 consisting of an amino acid sequence set forth in SEQ ID NO: 13
(d) Light chain CDR1 consisting of an amino acid sequence set forth in SEQ ID NO: 14
(e) Light chain CDR2 consisting of an amino acid sequence set forth in SEQ ID NO: 15
(f) Light chain CDR3 consisting of an amino acid sequence set forth in SEQ ID NO: 16

The heavy chain variable region of the MoAb1 antibody preferably has an amino acid sequence consisting of 119 amino acid residues and set forth in SEQ ID NO: 17, and the light chain variable region of the MoAb1 antibody preferably has an amino acid sequence consisting of 112 amino acid residues and set forth in SEQ ID NO: 18.

1. Immunochromatography

In general, an immunochromatographic (hereinafter, also referred to as chromatography) method is a technique of simply, rapidly, and specifically determining and measuring a test substance by the following technique. That is, an antibody-immobilized membrane (porous carrier) is used as an immobilized phase, where the antibody-immobilized membrane may have a label substance-trapping region having at least one detection site having an immobilization reagent (specifically, an antibody) capable of binding to a test substance. On this porous carrier, a liquid containing a label substance modified with a first antibody against a test substance is moved chromatographically as a moving layer to reach the label substance-trapping region having the detection site while the test substance and the label substance specifically bind to each other. The technique is a technique of qualitatively and quantitatively analyzing the presence of a test substance in a test specimen visually or using an appropriate device by utilizing that, in the detection site of the label substance-trapping region, a complex body of the test substance and the label substance specifically binds to an immobilized second antibody, and thereby the label substance is concentrated in the second antibody only in a case in which the test substance is present in a test specimen.

In a chromatographic method of the embodiment of the present invention, using two kinds of amplification reagents used for amplifying signals of a label substance, specifically, a compound containing silver and a reducing agent capable of reducing silver ions, it is possible to amplify signals by an amplification reaction using, as a nucleus, a complex body of a label substance and a test substance bound to an immobilization reagent on a label substance-trapping region, and as a result, it is possible to achieve high-sensitivity. According to the present invention, rapid chromatography with high-sensitivity can be performed.

2. Test Specimen

A test specimen that can be analyzed using the chromatographic method and the kit of the embodiment of the present invention is not particularly limited as long as it is a specimen that may contain a test substance. Examples thereof include biological specimens, particularly body fluids (for example, blood, serum, plasma, spinal fluid, tears, sweat, urine, pus, runny nose, or sputum) of animals (particularly humans), or excrements (for example, feces), organs, tissues, mucous membranes and skin, scraped test sample (swabs) that contain these substances, mouthwash, or animals and plants themselves or dried substances thereof. The test substance in the present invention is lipoarabinomannan, a partial structure of lipoarabinomannan, a *Mycobacterium tuberculosis* group or acid-fast *bacillus* group containing lipoarabinomannan, and the like.

3. Pretreatment of Test Specimen

In the chromatographic method of the embodiment of the present invention, it is possible to use the test specimen as it is, or in a form in which the test specimen has been concentrated by an appropriate method, in a form in which appropriate ingredients for pretreatment are added to the test specimen, in a form of an extraction liquid obtained by extracting the test specimen using an appropriate solvent for extraction, in a form of a diluent solution obtained by diluting an extraction liquid with an appropriate diluent, or in a form of in which an extraction liquid has been concentrated by an appropriate method. As the solvent for extraction used in the present invention, it is possible to use a solvent used in a general immunological analysis method (for example, water, physiological saline, a buffer solution, and the like), or a water-miscible organic solvent that enables performing of a direct antigen-antibody reaction by diluting with such a solvent.

4. Constitution

In the chromatographic kit of the embodiment of the present invention, a chromatographic strip can be incorporated and used. The chromatographic strip that can be used is not particularly limited as long as it is a chromatographic strip that can be used in general chromatographic methods.

The chromatographic strip that can be used in the present invention has a label substance-holding region and a label substance-trapping region from the upstream direction to the downstream direction of a spreading direction of a test specimen containing *Mycobacterium tuberculosis*. In a preferred aspect, the chromatographic strip further has a region containing a coloring reagent. A more preferred aspect of the present invention is an aspect in which the region containing a coloring reagent is located in the downstream direction of the label substance-trapping region. Furthermore, an aspect, in which a specimen-added pad, a label substance-holding pad having a label substance-holding region (for example, gold colloid antibody-holding pad), an antibody-immobilized membrane that is a porous carrier (for example, an antibody-immobilized membrane having a label substance-trapping region), and a water absorption pad are disposed in this order on a pressure-sensitive adhesion sheet, is preferably used. The antibody-immobilized membrane that is a porous carrier has a label substance-trapping region that is a region having at least one detection site on which an antibody that specifically binds to *Mycobacterium tuberculosis* is immobilized, or as desired, the antibody-immobilized membrane may further have a control site (sometimes referred to as a control region) which is a region in which an antibody for control or an antigen is immobilized.

The label substance-holding pad which has the label substance-holding region and can be used in the present invention can be prepared by preparing a suspension containing the label substance, applying the suspension to an appropriate water absorption pad (for example, glass fiber pad), and then drying the suspension.

4-1. Label Substance

As the label substance used in the present invention, it is preferable to use a label substance containing a metal as a label used for labeling the first antibody against lipoarabinomannan. The label substance is more preferably a metal particle. As the type of metal that can be used in the present invention, noble metals such as gold, silver, and platinum, iron, lead, copper, cadmium, bismuth, antimony, tin, or mercury can be preferably used, or compounds thereof can be used. Noble metals such as gold, silver, and platinum can be more preferably used. As a preferred form of the label substance containing a metal which can be used in the present invention, it is possible to use a metal colloid label or a metal sulfide label. In the present invention, as the metal colloid label, platinum colloid, gold colloid, silver colloid, iron colloid, aluminum hydroxide colloid, or the like can be preferably used, and as the metal sulfide label, each of sulfides of iron, silver, lead, copper, cadmium, bismuth, antimony, tin, or mercury can be preferably used. In the present invention, platinum colloid, gold colloid, or silver colloid can be more preferably used, and gold colloid can be most preferably used. In a case where gold colloid particles are used as the metal colloid label, commercially available gold colloid particles may be used. Alternatively, gold colloid particles can be prepared by a conventional method such as a method of reducing chlorauric acid with sodium citrate (Nature Physical Science, 241 (1973) 20, and the like).

An average particle size of the metal colloid is preferably about 1 nm to 500 nm, more preferably 3 to 100 nm, and particularly preferably 5 to 60 nm. An average particle size of the metal colloid used in the present invention can be measured with a commercially available particle size distribution meter or the like. As a method of measuring particle size distribution, optical microscopy, confocal laser microscopy, electron microscopy, atomic force microscopy, a static light scattering method, a laser diffraction method, a dynamic light scattering method, a centrifugal sedimentation method, an electric pulse measurement method, a chromatographic method, an ultrasonic attenuation method, and the like are known, and devices corresponding to the respective principles are commercially available.

As a method of measuring an average particle size, a dynamic light scattering method can be preferably used because of a particle size range and ease of measurement. Examples of commercially available measuring devices using dynamic light scattering include NANOTRAC UPA (Nikkiso Co., Ltd.), a dynamic light scattering type particle size distribution measuring device LB-550 (HORIBA, Ltd.), a concentrated particle size analyzer FPAR-1000 (Otsuka Electronics Co., Ltd.), and the like. In the present invention, an average particle size is obtained as a value of a median diameter (d=50) measured at a measurement temperature of 25° C.

According to the present invention, in chromatography using a metal colloid label or metal sulfide label, another metal alloy label (hereinafter sometimes referred to as a metallic label), or a metal-containing polymer particle label as a label substance for detection, signals of the metallic label can be amplified. Specifically, in a case where, after formation of a complex body of a test substance and a label for detection, silver ions supplied from a compound containing silver such as an inorganic silver salt or an organic silver salt are brought into contact with a reducing agent capable of reducing silver ions, the silver ions are reduced by the reducing agent, and thereby silver particles are generated, the silver particles are deposited on a metallic label with the metallic label as a nucleus, and therefore, the metallic label is amplified, and analysis of the test substance can be performed with high-sensitivity. That is, in the chromatographic method of the embodiment of the present invention, the silver particles generated by the reducing action of silver ions by the reducing agent are used to perform a reaction for depositing on a label of an immune complex body, and signals thus amplified are analyzed.

4-2. Antibody

The label substance is modified with the first antibody in the present invention. The chromatographic kit of the embodiment of the present invention includes the second antibody against lipoarabinomannan in a label substance-trapping region.

In the present invention, a method of modifying the label substance using the first antibody can be performed according to, for example, a conventionally known method described below (for example, The Journal of Histochemistry and Cytochemistry, 30, 7 (1982) 691-696) in a case of binding a metal colloid and an antibody to each other. As a specific example, a metal colloid and an antibody are mixed in an appropriate buffer solution at room temperature for 5 minutes or longer. After the reaction, a precipitate obtained by centrifugation is dispersed in a solution containing a dispersant such as polyethylene glycol, and thereby an antibody labeled with the metal colloid can be obtained.

4-3. Porous Carrier

As the porous carrier that can be used in the present invention, a nitrocellulose carrier (such as a nitrocellulose membrane), a cellulose membrane, an acetyl cellulose membrane, a polysulfone membrane, a polyether sulfone membrane, a nylon membrane, a glass fiber, a non-woven fabric, a cloth, a thread, and the like are particularly preferable.

In the present invention, a label substance-trapping region of the porous carrier has a detection site on which the second antibody against lipoarabinomannan is immobilized. The second antibody against lipoarabinomannan may be directly immobilized on a part of the porous carrier by a physical or chemical bond, and thereby the detection site is formed, or the second antibody may physically or chemically bind to fine particles such as latex particles, these fine particles are trapped on a part of the porous carrier and immobilized, and thereby the detection site is formed. The porous carrier is preferably used after immobilizing the second antibody against lipoarabinomannan thereon and then subjecting the porous carrier to a non-specific adsorption prevention treatment such as a treatment with an inactive protein. The porous carrier of the present invention can also be preferably used in a form of having a plurality of binding sites, and as desired, it may further have the above-mentioned control site as a part of the label substance-trapping region.

4-4. Label Substance-Holding Pad

In the present invention, an aspect in which a label substance-holding pad having a label substance-holding region, preferably a gold colloid-holding pad, is incorporated into the chromatographic kit and used is preferable. As a material of the label substance-holding pad, for example, cellulose filter paper, glass fiber, non-woven fabric, and the like can be preferably used, and it is possible to obtain the label substance-holding region by impregnating a certain amount of the label substance prepared as described above and drying it.

4-5. Specimen-Added Pad

It is preferable to use the chromatographic kit of the embodiment of the present invention by further incorporating a specimen-added pad thereto. For the specimen-added pad, an aspect in which the specimen-added pad has not only a function of receiving an added specimen containing a test substance but also has a function of filtering insoluble particles and the like in the specimen is preferable. Examples of materials of the specimen-added pad include materials having uniform characteristics such as cellulose filter paper, glass fibers, polyurethane, polyacetate, cellulose acetate, nylon, and cotton cloth. In addition, in order to prevent the test substance in the specimen from non-specifically adsorbing to a material of the specimen-added pad and lowering accuracy of analysis during analysis, a material forming the specimen-added pad can also be used after being treated to a non-specific adsorption prevention treatment in advance. In the present invention, the specimen-added pad may also serve as the label substance-holding pad having the label substance-holding region.

4-6. Water Absorption Pad

In the present invention, it is preferable to use the chromatographic kit by incorporating a water absorption pad thereto. The water absorption pad is a site that physically absorbs an added specimen by chromatographic migration and also absorbs and removes unreacted label substances that are insolubilized in a detection part of a chromatographic carrier, and water absorbent materials such as cellulose filter paper, non-woven fabric, cloth, and cellulose acetate are used. Because a chromatographic speed after a chromatographic tip end portion of the added specimen reaches the water absorption pad depends on materials, sizes, and the like of the water absorption pad, it is possible to set a speed that is suitable for measurement of the test substance by selecting materials, sizes, and the like of the water absorption pad.

5. Coloring Reagent for Detecting Reducing Agent Capable of Reducing Silver Ions In the chromatographic kit used in the present invention, a coloring reagent is preferably carried by a porous carrier.

In the present invention, it is preferable to use, for example, a compound that reacts with ions and develops color as the coloring reagent for detecting the reducing agent capable of reducing silver ions. Although a first amplification reagent will be described later in the present specification, a compound that reacts with $Fe^{2+}$ ions and develops color can be used as a coloring reagent for the first amplification reagent in a case where the first amplification reagent is a reagent containing divalent iron ions ($Fe^{2+}$), for example. As the compound that reacts with $Fe^{2+}$ ions and develops color, it is possible to use a compound capable of developing color by forming a complex with $Fe^{2+}$ ions. As specific examples of the compound that reacts with $Fe^{2+}$ ions and develops color, it is possible to use compounds having a phenanthroline skeleton [for example, 1,10-phenanthroline, 5-methyl phenanthroline, 5-nitrophenanthroline, bathophenanthroline (4,7-diphenyl-1,10-phenanthroline), bathophenanthroline disulfate, and the like], or compounds having a bipyridine skeleton [for example, 2,2'-bipyridine and the like], and compounds having a phenanthroline skeleton can be preferably used. In addition, in a case in which a pH of an aqueous solution containing a test specimen and a pH of an aqueous solution containing the first amplification reagent are different from each other, it is possible to preferably use a reagent in which tint is changed because of structural change occurring due to $H^+$ ions in order to detect the first amplification reagent. Particularly, in a case in which the aqueous solution containing the first amplification reagent is acidic (where a pH is lower than 7, and a concentration of $H^+$ ions is high), as an pH indicator for an acidic region, it is preferable to appropriately select compounds and the like (for example, diazo-based coloring reagents such as methyl orange, methyl red, congo red, and methyl yellow, and sultone-based coloring reagents such as thymol blue, bromocresol green, bromocresol purple, and bromothymol blue), which react with $H^+$ ions and develops color and which are well-known coloring reagents, in accordance with the pH of the aqueous solution containing the amplification reagent. Among them, 1,10-phenanthroline, bathophenanthroline, or bromocresol green can be more preferably used.

The coloring reagent is preferably a coloring reagent that does not substantially move in the porous carrier in a case where any of an aqueous solution containing a test specimen or an aqueous solution containing the reducing agent reducing silver ions is spread. Accordingly, Log P (partition coefficient in water and octanol) of the coloring reagent is preferably 4.0 or more, and more preferably 5.0 or more. An actual measurement value may be used as Log P, but a calculation value obtained from a chemical structure or the like can also be used as a simple judging method. As a method of calculating Log P, a calculation method used in ChemDraw Pro version 12 of Cambridge Soft is preferable. Responsiveness and Log P (according to ChemDraw Pro version 12) of representative coloring reagents are shown in Table 1.

TABLE 1

| Name of compound | Responsiveness | LogP |
|---|---|---|
| 2,2'-Bipyridine | $Fe^{2+}$ response | 1.88 |
| Bathophenanthroline disulfonic acid | $Fe^{2+}$ response | 0.52 |
| 1,10-Phenanthroline | $Fe^{2+}$ response | 2.2 |
| 5-Methylphenanthroline | $Fe^{2+}$ response | 2.69 |
| 5-Nitrophenanthroline | $Fe^{2+}$ response | 2.34 |
| Thymol blue | pH response | 4.01 |
| Methyl orange | pH response | 2.95 |
| Methyl red | pH response | 3.63 |
| Congo red | pH response | 3.63 |
| Methyl yellow | pH response | 4.76 |
| Bathophenanthroline | $Fe^{2+}$ response | 5.55 |
| Bromocresol green | pH response | 7.99 |
| Bromocresol purple | pH response | 6.33 |
| Bromothymol blue | pH response | 8.8 |

A region having the coloring reagent is preferably located downstream of the label substance-trapping region having the detection site of the porous carrier. As a method of holding the coloring reagent in the chromatographic kit, there are a method of immersing a water absorption pad to be described later in a coloring reagent solution and drying under reduced pressure, a method of linearly applying in a downstream direction from a label substance-trapping region of an insoluble carrier, and the like.

In a case where the coloring reagent substantially moves in the insoluble carrier in a case where the aqueous solution containing the test specimen or the aqueous solution containing the first amplification reagent is spread, it is preferable that the coloring reagent be contained in the water absorption pad and used.

In a case where the coloring reagent does not substantially move in the insoluble carrier in a case where the aqueous solution containing the test specimen or the aqueous solution containing the first amplification reagent is spread, it is preferable to cause the insoluble carrier having the label substance-trapping region to carry the coloring reagent.

In the present invention, an aspect in which the coloring reagent is carried by the insoluble carrier is more preferable because then it is possible to display arrival of the first amplification reagent in the label substance-trapping region with a smaller time lag.

In the present invention, in a case where a region to which a test specimen containing a test substance is added, and a label substance-trapping region are provided in this order from an upstream direction to a downstream direction with respect to a spreading direction of the test specimen containing the test substance, an upstream direction and a downstream direction with respect to the spreading direction of the test specimen containing the test substance are defined in a case where the test specimen is spread by utilizing a capillary phenomenon, suction power in a case where the water absorption pad is used, or the like. In a specific aspect of the present invention, in a case where a test specimen and the like are spread from a label substance-holding region toward a label substance-trapping region, a direction of the label substance-holding region is defined as an upstream direction, and a direction of the label substance-trapping region is defined as a downstream direction.

In a preferred aspect of the present invention, the first amplification reagent of the two kinds of amplification reagents used for amplifying signals of a label substance trapped in the label substance-trapping region is spread from the upstream direction of the label substance-trapping region to the downstream direction of the label substance-trapping region to detect physical or chemical changes in the region having the coloring reagent, and thereby it is possible to confirm that the label substance-trapping region is filled with the first amplification reagent. As the physical or chemical changes in the region having the coloring reagent, it is possible to detect changes in color development or fluorescence caused by a reaction between the first amplification reagent and the coloring reagent. Color development can be preferably detected.

Such physical or chemical changes may be detected visually or may be detected using a detection device.

6. Method for Immunological Test

A sandwich method which is a specific embodiment for the chromatographic method of the embodiment of the present invention will be described below.

The sandwich method is not particularly limited, but for example, analysis of a test substance can be performed by the following procedure. First, a first antibody against lipoarabinomannan and a second antibody against lipoarabinomannan are prepared in advance. In addition, label substances are modified with the first antibody in advance. In a case where the second antibody is immobilized on an appropriate chromatographic carrier (porous carrier) (for example, nitrocellulose membrane, glass fiber membrane, nylon membrane, cellulose membrane, and the like) so as to serve as a label substance-trapping region, and this region is brought into contact with a test specimen (or an extraction liquid thereof) that may contain lipoarabinomannan, binding to the second antibody (for example, an antigen-antibody reaction with the second antibody) occurs in a case where lipoarabinomannan is present in the test specimen. In a case where an excess amount of label substances modified with the first antibody is further brought into contact with the region at the same time of binding of the test substance and the second antibody, or after binding thereof, a complex body consisting of the immobilized second antibody, lipoarabinomannan, and the label substances modified with the first antibody is formed in a case where lipoarabinomannan is present in the test specimen.

In the sandwich method, it is possible to determine the presence or absence of the test substance in the test specimen or measure an amount thereof by removing a label substance that did not form an immune complex body after the reaction of the immobilized second antibody with lipoarabinomannan, and lipoarabinomannan with the first antibody with which the label substances are modified is completed, and thereafter, by for example, observing a label substance-trapping region of an insoluble carrier as it is, and detecting or quantitatively determining a label substance. In the present invention, for example, a reducing agent and a silver ion-containing compound are supplied, and thereby signals from a label substance that has formed such a complex body are amplified and detected.

7. Amplification Reagent

An amplification reagent is a reagent that can cause signal amplification by catalytically reacting due to an action of a label substance or a test substance and causing coloration of a compound, luminescence, and the like. The amplification reagent can used in a state of a solution containing a reagent, that is, an amplification liquid. Examples thereof include a silver ion solution that causes metal silver to precipitate on a metal label by physical development, a solution of a phenylenediamine compound and a naphthol compound which serves as a colorant due to an action of a peroxidase label and hydrogen peroxide, and the like.

For details, a so-called developer can be used as an amplification liquid containing an amplification reagent, where developers are described in general books in the field of photographic chemistry (for example, "Fundamentals of Photograph Engineering (Revised)—Silver Halide Photography—" (edited by the Society of Photography and Imaging of Japan, Corona Publishing Co., Ltd.), "Chemistry of Photography" (by Akira SASAI, Shashinkogyo Publishing Company), and "Latest Prescription Handbook" (by Shinichi KIKUCHI et al., Amiko Publishing Company)). It is possible to use any developer as an amplification liquid without particular limitation as long as it is a so-called physical developer which contains silver ions in the liquid and in which the silver ions in the liquid are reduced mainly by metal colloids and the like which form the core of development.

In the present invention, two kinds of amplification reagents are used. It is preferable that a first amplification reagent be incorporated in a first amplification liquid, and a second amplification reagent be incorporated in a second amplification liquid among the two kinds of amplification reagents used for amplifying signals of label substances trapped in the label substance-trapping region, and amplification be performed by adding the first amplification liquid and the second amplification liquid in this order. The first amplification liquid is preferably added to a pad which is for liquid sending of a reducing agent solution and is located in an upstream direction of a label substance-holding pad and a specimen-added pad.

As a specific example of the amplification liquid, it is possible to use a combination of a first amplification liquid containing a reducing agent capable of reducing silver ions and a second amplification liquid containing a compound containing silver.

Hereinafter, the reducing agent capable of reducing silver ions contained in the first amplification liquid, and the compound containing silver contained in the second amplification liquid will be described.

7-1. Compound Containing Silver

As the compound containing silver, it is possible to use silver ion-containing compounds such as organic silver salts, inorganic silver salts, or silver complexes. The compound is preferably a silver ion-containing compound having a high solubility in solvents such as water, and examples thereof include silver nitrate, silver acetate, silver lactate, silver butyrate, silver thiosulfate, and the like. Silver nitrate is particularly preferred. Silver complexes are preferably silver complexes coordinated with ligands having a water-soluble group such as a hydroxyl group or a sulfone group, and examples thereof include silver hydroxythioether and the like.

In general, as silver, inorganic silver salts or silver complexes are contained in an amount of 0.001 mol/m$^2$ to 0.2 mol/m$^2$, and are preferably contained in an amount of 0.01 mol/m$^2$ to 0.05 mol/m$^2$.

7-2. Reducing Agent Capable of Reducing Silver Ions

As the reducing agent capable of reducing silver ions, any inorganic or organic material or a mixture thereof can be used as long as it can reduce silver ions to silver.

Preferred examples of inorganic reducing agents include reducing metal salts and reducing metal complex salts which are capable of changing an atomic value with metal ions such as $Fe^{2+}$, $V^{2+}$, or $Ti^{3+}$. In a case in which an inorganic reducing agent is used, it is necessary to remove or detoxify oxidized ions by complexing or reducing the oxidized ions. For example, in a system in which $Fe^{2+}$ is used as a reducing agent, a complex of $Fe^{2+}$, which is an oxide, can be formed using citric acid or EDTA and detoxified. In the present system, such an inorganic reducing agent is preferably used, and a metal salt of $Fe^{2+}$ is more preferred.

It is also possible to use a main developing agent used in a light-sensitive silver halide photographic material of a wet-type (such as methyl gallate, hydroquinone, substituted hydroquinone, 3-pyrazolidones, p-aminophenols, p-phenylenediamines, hindered phenols, amidoximes, azines, catechols, pyrogallols, ascorbic acid (or derivatives thereof), and leuco colorants), and other materials obvious to those who are skilled in the technology in the present field, such as a material disclosed in U.S. Pat. No. 6,020,117A.

As the reducing agent, an ascorbic acid reducing agent is also preferable. Useful ascorbic acid reducing agents include ascorbic acid and analogs thereof, and isomers and derivatives thereof. Preferred examples thereof include D- or L-ascorbic acid and sugar derivatives thereof (such as γ-lactoascorbic acid, glucoascorbic acid, fucoascorbic acid, glucoheptoascorbic acid, and maltoascorbic acid), a sodium salt of ascorbic acid, a potassium salt of ascorbic acid, isoascorbic acid (or L-erythroascorbic acid), a salt thereof (such as alkali metal salts, ammonium salts, or salts known in the technical field), ascorbic acid of the enediol type, ascorbic acid of the enaminol type, ascorbic acid of the thioenol type, and the like.

Particularly preferred examples thereof include D-, L-, or D,L-ascorbic acid (and an alkali metal salt thereof) or isoascorbic acid (or an alkali metal salt thereof), and a sodium salt is a preferable salt. A mixture of these reducing agents can be used as necessary.

8. Other Auxiliaries

As other auxiliaries of the amplification liquid, buffers, preservatives such as antioxidants or organic stabilizers, and rate regulators may be included. As the buffer, it is possible to use, for example, acetic acid, citric acid, sodium hydroxide, or salts of any of these substances, or a buffer formed of tris(hydroxymethyl)aminomethane or other buffers used in general chemical experiments. A pH can be adjusted to an optimum pH for the amplification liquid by appropriately using these buffers. Furthermore, an alkylamine can be used as an additive as an antifogging agent, and dodecylamine is particularly preferable. In addition, a surfactant can be used in order to improve solubility of these additives, and $C_9H_{19}$—$C_6H_4$—O—$(CH_2CH_2O)_{50}$H is particularly preferable.

As a method of spotting the amplification reagent on the chromatographic kit, a method is preferable in which a reducing agent solution as the first amplification liquid is spotted on a pad for liquid sending of the reducing agent solution, a silver ion solution as the second amplification liquid is spotted from above on a region including a label substance-trapping region, and the silver ion solution is infiltrated in a thickness direction of an insoluble carrier.

As a method of incorporating the two kinds of amplification reagents into the chromatographic kit, there is a method of disposing a pot containing a solution containing each of the amplification reagents above a site at which each of the amplification reagents is spotted. It is preferable that the reducing agent solution (first amplification liquid) be placed on the pad for liquid sending of the reducing agent solution, and the pot containing the silver ion solution (second amplification liquid) be placed immediately above a hole filled with the silver ion solution. By disposing in this manner, the liquid flows by pushing each pot and can be spotted on a predetermined site.

Immunochromatographic Kit

In the immunochromatographic kit of the embodiment of the present invention, the label substance modified with the first antibody against lipoarabinomannan may be provided on the porous carrier in advance, or alternatively, the label substance modified with the first antibody against lipoarabinomannan may be provided separately from the porous carrier. In this case, the label substance modified with the first antibody against lipoarabinomannan, which is provided separately from the porous carrier, can be measured by a method such as a method of mixing the label substance with a test specimen and then spreading the mixture on the porous carrier.

The immunochromatographic kit of the embodiment of the present invention further includes the compound containing silver and the reducing agent capable of reducing silver ions.

The immunochromatographic kit of the embodiment of the present invention may include a housing case including, therein, the porous carrier having a reaction site, the compound containing silver, and the reducing agent capable of reducing silver ions.

The immunochromatographic kit of the embodiment of the present invention may further include pots each having a tearable member, in which the compound containing silver and the reducing agent capable of reducing silver ions may be respectively sealed in the pots. In this case, the pots can be broken by an external force.

Figure 2:
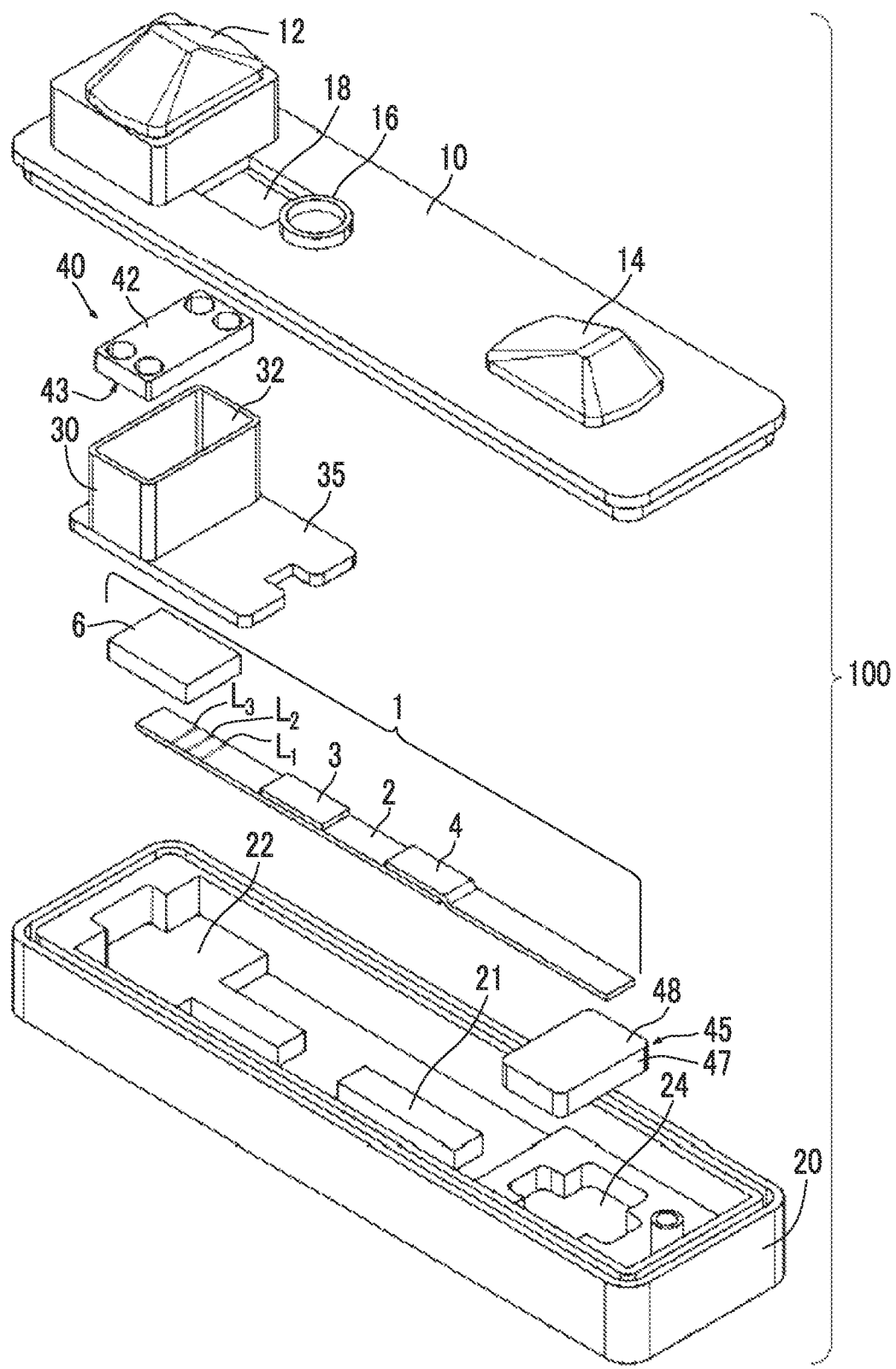
FIG. 2 is an exploded schematic perspective view showing the example of the immunochromatographic kit.

FIG. 1 is an exploded schematic perspective view illustrating an immunochromatographic kit 100 showing an example of the present invention, and FIG. 2 is an exploded schematic perspective view of the immunochromatographic kit 100 of FIG. 1.

As illustrated in FIG. 1 and FIG. 2, in the immunochromatographic kit 100 of the present embodiment, a housing case 9 includes an inspection strip 1 that has an porous carrier 2 having an inspection region of a test substance and is for spreading a specimen liquid, and a first pot 40 and a second pot 45 which are for amplifying a detection signal in the inspection region, which respectively include a surface having a sheet member, and in which a first amplification liquid 41 and a second amplification liquid 46 are sealed, respectively. The housing case 9 includes a lower case 20 having an accommodation portion 21 in which the inspection strip 1 is disposed, an upper case 10 joined to the lower case 20 along a peripheral edge, and a middle member 30 disposed between the upper case 10 and the lower case 20. In explaining the immunochromatographic kit 100, the upper case 10 side is defined as an upper part and the lower case 20 side is defined as a lower part.

The middle member 30 has a first pot accommodation portion 32 which accommodates the first pot 40 and which has, on a bottom surface, an amplification liquid-filled hole for dropwise addition of the first amplification liquid 41 onto the porous carrier 2. In addition, a protrusive tearing portion 34 that tears up a sheet member 43 is provided at a location facing the sheet member 43 of the first pot 40 in the first pot accommodation portion 32. In the present example, the first pot 40 is disposed above the first pot accommodation portion 32 so that the surface having the sheet member 43 is the lower surface, and the tearing portion 34 is provided on the bottom surface of the first pot accommodation portion 32 facing the sheet member 43 (refer to FIG. 3).

In addition, a flow path-forming portion 35 is provided so as to extend to a downstream side of the bottom surface of the first pot accommodation portion 32 of the middle member 30. The flow path-forming portion 35 is disposed to correspond with positions above an inspection region $L_1$, a confirmation region $L_2$, and an amplification label region $L_3$, and is formed of a transparent material so that these regions $L_1$ to $L_3$ can be visually checked.

The upper case 10 includes, on a part facing the first pot 40, a first protrusive deforming portion 12 that is deformed towards the first pot 40 side so as to allow the tearing portion 34 of the middle member 30 to tear up the sheet member 43 of the first pot 40 by application of a pressing force from the outside. In addition, the upper case 10 includes, on a part facing the second pot 45, a second protrusive deforming portion 14 that is deformed towards the second pot 45 side so that a sheet member 48 of the second pot 45 is torn up by application of a pressing force from the outside.

In addition, a hole 16 for dropwise addition of a specimen liquid is provided on the upper case 10, and a specimen liquid is added dropwise onto a label-holding pad 3 of the inspection strip 1 from this hole 16. In a case where a location of the label-holding pad 3 is adjusted so that locations of the hole 16 and the label-holding pad 3 correspond to each other, it is possible to reliably spot the specimen liquid onto the label-holding pad 3. In addition, the upper case 10 includes an observation window 18 for visually checking the three regions $L_1$ to $L_3$ at positions corresponding to the flow path-forming portion 35 of the middle member 30.

In the lower case 20, as an accommodation portion in which the inspection strip 1 is disposed, a porous carrier accommodation portion 21 on which the porous carrier 2 is mounted is provided, and an absorption pad accommodation portion 22 on which an absorption pad 6 is mounted is provided on the downstream side of the porous carrier accommodation portion. In addition, a second pot accommodation portion 24 in which the second pot 45 is accommodated is provided on the upstream side of the porous carrier accommodation portion 21.

Figure 3:
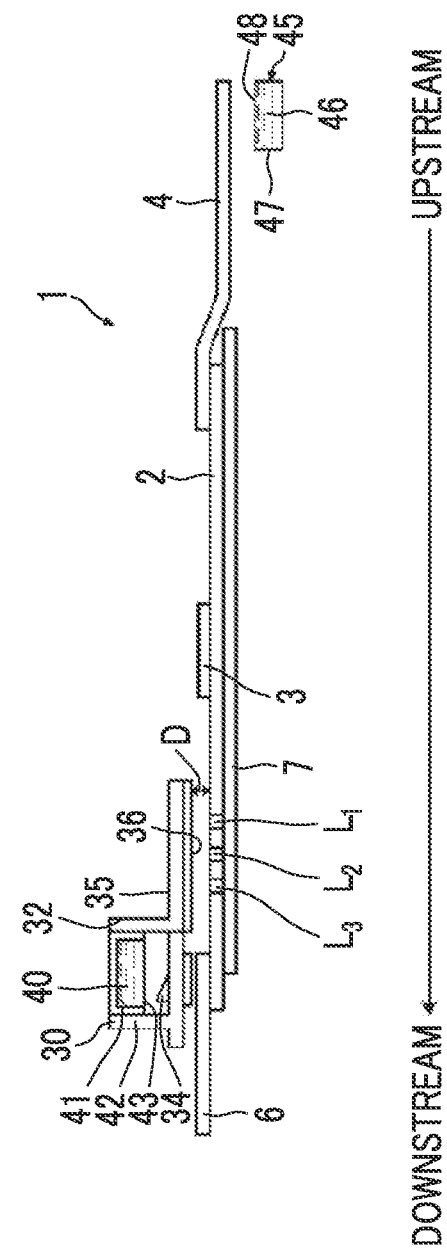
FIG. 3 is a schematic side view showing a positional relationship between an inspection strip, and a first pot and a second pot.

FIG. 3 is a schematic side view illustrating a positional relationship between the inspection strip 1, the middle member 30, and the two pots 40 and 45. As illustrated in FIG. 3, the inspection strip 1 includes the porous carrier 2 spreading the specimen liquid, the label-holding pad 3 having a label substance modified with an antibody immobilized on the porous carrier 2, a liquid-sending pad 4 which is disposed in contact with one end of the porous carrier 2 and sends the second amplification liquid 46 to the porous carrier 2, and the absorption pad 6 disposed in contact with the other end of the porous carrier 2. The porous carrier 2 is immobilized to and supported by a back pressure-sensitive adhesion sheet 7. In addition, between the label-holding pad 3 and the absorption pad 6, the porous carrier 2 has the inspection region $L_1$, the confirmation region $L_2$, and the amplification label region $L_3$ in this order from the label-holding pad 3 side.

In the present specification, there are cases in which the porous carrier 2, which has the inspection region $L_1$, the confirmation region $L_2$, and the amplification label region $L_3$ formed thereon, is referred to as a chromatographic carrier. In addition, in the present specification, as illustrated in FIG. 3, the liquid-sending pad 4 side is defined as an upstream side and the absorption pad 6 side is defined as a downstream side.

The middle member 30 is positioned at the upper portion and the downstream end side of the inspection strip 1, and the first pot 40 is disposed in the first pot accommodation portion 32 of the middle member 30 with the sheet member 43 facing downward. The second pot 45 is accommodated at the lower portion and the upstream end of the inspection strip 1 in the lower case 20 with the sheet member 48 facing upward.

As shown in FIG. 3, a gap (clearance) D is formed between a rear surface 36 of the flow path-forming portion 35 of the middle member 30, and the porous carrier 2 of the inspection strip 1. The gap D is preferably within a range of 0.01 mm to 1 mm. In a case where the gap is 0.01 mm or more, an amplification liquid and the like can be sufficiently infiltrated, and in a case where the gap is 1 mm or less, capillary force is exerted and the gap between the porous carrier 2 and the middle member 30 can be uniformly filled with the first amplification liquid 41.

In the first pot 40 in which the first amplification liquid 41 is sealed, for example, a container 42 which is formed of a resin material and has an opening on one surface is filled with the first amplification liquid 41, and the opening of the container 42 is covered with the tearable sheet member 43 and sealed.

Similarly, in the second pot 45 in which the second amplification liquid 46 is sealed, for example, a container 47 which is formed of a resin material and has an opening on one surface is filled with the second amplification liquid 46, and the opening of the container 47 is covered with the tearable sheet member 48 and sealed.

As the tearable sheet members 43 and 48 in the first pot 40 and the second pot 45, laminate films such as aluminum foils and aluminum sheets are suitability used. The term "tear" refers to a state in which the sheet does not regenerate after being torn up.

10. Method of Calculating Average Particle Size of Label Substance in Detection

In detection (after amplification), a test line portion is cut out, a rear surface of a specimen is attached to a specimen stand with carbon paste, and thereafter, a cross section is cut, carbon vapor deposition is performed, and a shape and a size are observed with a scanning electron microscope. For example, observation of a specimen surface by reflected electrons at an accelerating voltage of 10 KV using a FE-STEM S-5500 manufactured by Hitachi High-Technologies Corporation can be performed with a scanning electron microscope (SEM). Thereafter, 100 signal particles are selected, a circle equivalent diameter of a projected area of the particles is measured, and an average value is calculated and used for an average particle size in the detection.

An average particle size of the label substance in the detection is preferably 1 μm or more and 20 μm or less, and more preferably 3 μm or more and 20 μm or less.

Hereinafter, the present invention will be described more specifically with reference to Examples of the present invention. In the following Examples, materials, amounts used, ratios, details of a treatment, treatment procedures, and the like may be appropriately changed without departing from the gist of the present invention. Accordingly, the scope of the present invention should not be limitedly interpreted by the following specific examples.

EXAMPLES

Immunochromatographic kits of an example and a comparative example are *Mycobacterium tuberculosis* antigens-detecting immunochromatographic kits which are for detecting lipoarabinomannan antigens as a test substance.

(1) Production of Immunochromatographic Kit (1-1) Production of Anti-Lipoarabinomannan Antibody-Modified Gold Colloid as Label Substance Modified with First Substance that can Bind to Test Substance 1 mL of a 50 mmol/L of $KH_2PO_4$ buffer (pH 8.0) was added to 9 mL of a solution (Product No.: EM. GC50, manufactured by Boston Biomedical Inc.) containing gold colloid having a diameter of 50 nm to adjust a pH. Thereafter, 1 mL of a solution containing 20 µg/mL of an anti-lipoarabinomannan monoclonal antibody (antibody A194-01 produced according to a method for producing A-194-01 described in WO2017/139153A (DETAILED DESCRIPTION D. Anti-LAM and Anti-PIM6/LAM Antibodies 1. A194-01)) was added thereto and stirred for 10 minutes. Thereafter, after the solution mixture was left to stand for ten minutes, 550 µL of an aqueous solution containing 1 mass % polyethylene glycol (PEG; weight-average molecular weight (Mw.): 20,000, Product No. 168-11285, manufactured by FUJIFILM Wako Pure Chemical Corporation) was added to the solution mixture and stirred for 10 minutes. Subsequently, 1.1 mL of an aqueous solution of 10 mass % bovine serum albumin (BSA; Fraction V, Product No.: A-7906, manufactured by Sigma-Aldrich Co. LLC.) was added thereto and stirred for 10 minutes. This solution was centrifuged for 30 minutes under conditions of 8,000×g at 4° C. using a centrifugal separator (himacCF16RX, manufactured by Hitachi Ltd.). The supernatant liquid was removed with 1 mL thereof remaining at the bottom of a container, and gold colloid contained in the 1 mL solution remaining at the bottom of the container was re-dispersed by an ultrasonic washer. Thereafter, the solution was dispersed in 20 mL of a gold colloid preservative solution (20 mmol/L Tris-HCl (tris hydrochloric acid) buffer (pH 8.2), 0.05% PEG (Mw: 20,000), 150 mmol/L NaCl, 1% BSA), and was centrifuged again under the same conditions using the same centrifugal separator. Thereafter, the supernatant liquid was removed, ultrasonic dispersion was performed, and then the solution was dispersed in the gold colloid preservative solution. Thereby, an antibody-modified gold colloid (50 nm) solution was obtained.

(1-2) Production of Anti-Lipoarabinomannan Antibody-Modified Gold Colloid-Holding Pad as Label-Holding Pad The anti-lipoarabinomannan antibody-modified gold colloid produced in (1-1) was diluted with water so that a concentration of a Tris-HCl buffer (pH: 8.2) reached 20 mmol/L, a concentration of PEG (Mw: 20,000) reached 0.05 mass %, a concentration of sucrose reached 5 mass %, and an optical density of the gold colloid at 520 nm reached 0.1 in a case where an optical path length was set to 10 mm, and thereby a gold colloid coating liquid was obtained. This coating liquid was uniformly applied onto glass fiber pads each cut into 5 mm×300 mm (Glass Fiber Conjugate Pad, manufactured by EMD Millipore Corporation) by 1 mL per pad, and was dried at reduced pressure for 24 hours. Thereby an anti-lipoarabinomannan antibody-modified gold colloid-holding pad was obtained.

(1-3) Production of Test Sample Adjustment Reagent

A 800 mmol/L Tricine buffer solution (pH 8.5) (347-02844, manufactured by FUJIFILM Wako Pure Chemical Corporation) containing 0.2 wt % casein (030-01505, manufactured by FUJIFILM Wako Pure Chemical Corporation) and 2 wt % TWEENX® 40 polyoxyethylene sorbitan monopalmitate (T2531, manufactured by Tokyo Chemical Industry Co., Ltd.) was prepared, and 50 µL of this buffer solution was added into a tube for test sample preparation (Trust Medical Inc.). After drying the buffer solution in an environment of 25° C. and 10% Rh (relative humidity) or less for 3 days, drying was performed under reduced pressure for 24 hours, and thereby a solid state was obtained. Because 200 µL of the test sample was used in a case of use, final concentrations of each of the substances were 0.05 wt % casein, 0.5 wt % TWEEN® 40 polyoxyethylene sorbitan monopalmitate, and 200 mmol/L Tricine buffer solution (pH 8.5).

The anti-lipoarabinomannan antibody-modified gold colloid-holding pad produced in (1-2) as a label-holding pad was cut into 4 mm×5 mm pieces. The pieces were put in the above-mentioned tube one by one, and the tube was sealed using a heat sealing sealer (Toppan Printing Co., Ltd.).

(1-4) Production of Chromatographic Carrier

Using nitrocellulose membrane cut into 60 mm×300 mm (with a plastic backing, HiFlow Plus HF135 (capillary flow rate=135 sec/cm), manufactured by EMD Millipore Corporation) as a porous carrier, an inspection region, a confirmation region, and an amplification label region were formed on this membrane by a method described below, and thereby a chromatographic carrier was produced.

An anti-lipoarabinomannan monoclonal antibody (an antibody obtained by producing an antibody having a sequence described as MoAb1 in WO2013/129634A according to (4-1) Production of divalent antibody of 4. Measurement method in [Examples 5 to 12]) solution, which was prepared so that a concentration was 1.5 mg/mL, was applied in a line shape at a position 15 mm from the downstream side of a 60 mm short side of the nitrocellulose membrane, and thereby the inspection region was produced. Furthermore, an anti-human IgG antibody (anti-human IgG (H+L), rabbit F(ab')2, Product No. 309-006-003, manufactured by FUJIFILM Wako Pure Chemical Corporation) solution, which was prepared so that a concentration was 0.5 mg/mL, was applied in a line shape at a position 11 mm from the downstream side of the 60 mm short side, and thereby the confirmation region was obtained. Furthermore, a Bromocresol Green (manufactured by FUJIFILM Wako Pure Chemical Corporation), which was prepared so that a concentration was 30 mmol/L, was applied in a line shape at a position 9 mm from the downstream side of the 60 mm short side, and thereby the amplification label region was obtained. After the application of the respective solutions, the nitrocellulose membrane was dried at 50° C. for 30 minutes using a warm air-type dryer. After completion of the drying, the nitrocellulose membrane dried as described above was immersed in a vat in which 500 mL of a blocking liquid (50 mmol/L of a boric acid buffer (pH: 8.5) containing 0.5 mass % casein (derived from milk, Product No. 030-01505, manufactured by FUJIFILM Wako Pure Chemical Corporation)) was put, and the membrane was left to stand for 30 minutes. Thereafter, the nitrocellulose membrane was taken out, the nitrocellulose membrane was immersed in 500 mL of a washing and stabilizing liquid (50 mmol/L Tris-HCl buffer (pH: 7.5) containing 0.5 mass % sucrose and 0.05 mass % sodium cholate) prepared in another vat, and the membrane was left to stand for 30 minutes. Thereafter, the nitrocellulose membrane was removed from the liquid and dried at an environment of 25° C. for 24 hours.

A part to which the anti-lipoarabinomannan antibody was immobilized corresponded to the inspection region including the second substance binding to the test substance, a part to which the anti-human IgG antibody was immobilized corresponded to the confirmation region including the substance that can bind to the first substance, and a part to which the bromocresol green was immobilized corresponded to the amplification label region including the substance reacting with the first amplification liquid.

(1-5) Production of Inspection Strip

The chromatographic carrier produced in (1-4) was attached to a back pressure-sensitive adhesion sheet (60 mm×300 mm (manufactured by Adhesives Research)). Next, a 3 mm wide double-sided tape (NITTO DENKO CORPORATION) was fixed at a position 26 mm from the downstream side of a short side of the chromatographic carrier. Thereafter, the gold colloid-holding pad was fixed to the chromatographic carrier so that the downstream end of the double-sided tape and the downstream end of the glass fiber pad (Glass Fiber Conjugate Pad, manufactured by EMD Millipore Corporation) cut into 8 mm×300 mm overlapped each other. A liquid-sending pad (glass fiber pad cut into 25 mm×300 mm (Glass Fiber Conjugate Pad, manufactured by EMD Millipore Corporation) was attached to the upstream side of the chromatographic carrier so that the liquid-sending pad and the chromatographic carrier overlapped each other by 7 mm. Using a guillotine style cutter (CM4000, manufactured by NTC/NIPPN TechnoCluster, Inc.), a member produced in this manner was cut parallel to a direction perpendicular to a 300 mm long side such that a width was 5 mm. Thereby, 60 inspection strips (however, no absorption pads were included) were produced.

(1-6) Production of Amplification Liquid (1-6-1) Production of Amplification Liquid (Reducing Agent Solution) Sealed in Second Pot 23.6 mL of an aqueous solution of 1 mol/L iron nitrate produced by dissolving iron (111) nitrate nonahydrate (manufactured by FUJIFILM Wako Pure Chemical Corporation, 095-00995) in water, and 13.1 g of citric acid (manufactured by FUJIFILM Wako Pure Chemical Corporation, 038-06925) were dissolved in 290 g of water. After the substances were fully dissolved, 36 mL of a nitric acid (10 wt %) solution was added thereto while stirring the solution using a stirrer, and 60.8 g of iron (II) ammonium sulfate hexahydrate (manufactured by FUJIFILM Wako Pure Chemical Corporation, 091-00855) was added thereto. The solution thus prepared was used for a reducing agent solution which was the second amplification liquid sealed in the second pot.

(1-6-2) Production of Amplification Liquid (Silver Ion Solution) Sealed in First Pot 8 mL of a silver nitrate solution (including 10 g of silver nitrate) and 24 mL of an aqueous solution of 1 mol/L iron nitrate were added to 66 g of water. Furthermore, this solution was mixed with a solution obtained by dissolving 5.9 mL of nitric acid (10 wt %), 0.1 g of dodecylamine (manufactured by FUJIFILM Wako Pure Chemical Corporation, 123-00246), and 0.1 g of a surfactant $C_{12}H_{25}$—$C_6H_4$—O—$(CH_2CH_2O)_{50}$H in 47.6 g of water in advance. This mixed solution was used for a silver ion solution which was the first amplification liquid sealed in the first pot.

(1-7) Production of Absorption Pad 60 glass fiber pads each cut into 12 mm×10 mm (glass filter paper, manufactured by Advantech Co., Ltd.) were prepared and used for absorption pads.

(1-8) Production of Components of Immunochromatographic Kit

The lower case 20, the upper case 10, the middle member 30, the first pot 40, and the second pot 45 constituting the immunochromatographic kit 100 shown in FIGS. 1 to 3 were respectively produced by injection molding using polypropylene as a material. The upper case was produced by injection molding using, as a material, polypropylene containing 50 mass % of TAFTHREN (registered trademark) which is an olefinic elastomer manufactured by Sumitomo Chemical Co., Ltd. The uppercase 10 has two deformable portions (first protrusive deforming portion and second protrusive deforming portion). These two deforming portions are parts not separated from the upper case 10, and the upper case was produced by injection molding with the entire boundary as a part of the upper case 10.

In the upper case of the example, the first protrusive deforming portion 12 shown in FIGS. 1 and 2 has two protrusion portions, and the second protrusive deforming portion 14 has one protrusion portion.

(1-9) Production of Immunochromatographic Kit of Example

The lower case 20, the inspection strip produced in (1-5), and the absorption pad 6 produced in (1-7) were fixed as illustrated in FIGS. 1 to 3. Next, the first pot 40 and the second pot 45 were respectively filled with the first amplification liquid 41 to be sealed in the first pot 40 produced in (1-6-2) and the second amplification liquid 46 to be sealed in the second pot 45 produced in (1-6-1). The second pot 45 was sealed with aluminum foil as the sheet member 48, and the first pot 40 was sealed with aluminum foil as the sheet member 43. As shown in FIGS. 1 to 3, the second pot 45 was attached to the lower case 20 with the sheet member 48 facing upward, and the first pot 40 was attached to the middle member 30 with the sheet member 43 facing downward. In addition, in a state in which the upper case 10 and the lower case 20 were fitted so that the outer peripheries thereof came in contact with each other, contact portions of the upper case and the lower case were joined by ultrasonic welding. In this case, it was confirmed that the entire portions of the welded portions were uniformly welded in a sealed state. The immunochromatographic kit was produced in this manner.

(1-10) Comparative Example

As a comparative example, Alere Determine TB LAM Ag (Alere Inc.) was used for a *Mycobacterium tuberculosis* antigens-detecting immunochromatographic kit which is for detecting a lipoarabinomannan antigen as a commercially available test substance.

(2) Evaluation 1: Evaluation of Detection Sensitivity (2-1) Preparation of Test Sample Liquid Lipoarabinomannan (02249-61, NACALAI TESQUE, INC.) extracted from *Mycobacterium tuberculosis* was added to a urine test sample pooled from a urine test sample of a healthy person (BioreclamationiVT), and a test sample liquid at each lipoarabinomannan concentration was prepared.

(2-2) Measurement Using Comparative Example

According to the method of use of the comparative example, 60 μL of the test sample was spotted on the kit and reacted for 25 minutes. Whether a result was positive or negative was visually determined after completion of the reaction. A degree of coloration in a case of visually observing the confirmation region having a line shape was discriminated as follows: "+++" for deep coloration, "++" for coloration, "+" for light coloration, and "−" for no coloration. A lowest concentration that enabled discrimination was defined as a minimum detection sensitivity.

(2-3) Measurement Using Example

200 µL of the test sample was added to the test sample adjustment reagent and reacted for 40 minutes. After completion of the reaction, 40 µL of the test sample was spotted on the kit from the tube containing the test sample adjustment reagent.

Immediately after spotting the test sample, the aluminum foil, which is the sheet member 48 sealing the second amplification liquid 46 sealed in the second pot 45, was torn up by pressing down the second protrusive deforming portion 14, the liquid-sending pad 4 was immersed in the second pot 45, and thereby the second amplification liquid 46 was supplied to the porous carrier 2 utilizing a capillarity.

After discoloration of the amplification label region $L_3$ from green to orange, the first protrusive deforming portion 12 (first protrusive deforming portion 114 in Example) was pressed down to move the first pot 40 toward the tearing portion 34 of the first pot accommodation portion 32 of the middle member 30, and thereby the tearing portion 34 was caused to press and tear up the aluminum foil which is the sheet member 43 sealing the first pot 40. The silver ion solution which is the first amplification liquid 41 was supplied to the porous carrier 2 from the opening portion of the middle member 30, and thereby a silver amplification reaction was caused. The silver amplification reaction was completed in tens of seconds.

Whether a result was positive or negative was visually determined after completion of the silver amplification reaction. Regarding determination, a degree of coloration, which increases or decreases in proportion to an amount of lipoarabinomannan, at a line onto which the anti-lipoarabinomannan monoclonal antibody was applied was judged with naked eyes. A degree of coloration in a case of visually observing the confirmation region having a line shape was discriminated as follows: "+++" for deep coloration, "++" for coloration, "+" for light coloration, and "−" for no coloration. A lowest concentration that enabled discrimination was defined as a minimum detection sensitivity.

In addition, an average particle size of labeled particles after the completion of the silver amplification reaction was calculated using a scanning electron microscope (FE-STEM S-5500 manufactured by Hitachi High-Technologies Corporation), and it was found to be 10 µm.

(3) Result 1

Table 2 shows results of Evaluation 1.

TABLE 2

| Amount of LAM [ng/mL] | Comparative Example | Example 1 |
|---|---|---|
| 10 | +++ | No measurement |
| 1 | + | No measurement |
| 0.5 | + | No measurement |
| 0.4 | No measurement | ++ |
| 0.25 | + | No measurement |
| 0.2 | No measurement | ++ |

TABLE 2-continued

| Amount of LAM [ng/mL] | Comparative Example | Example 1 |
|---|---|---|
| 0.1 | − | + |
| 0.05 | No measurement | + |
| 0.025 | No measurement | − |
| 0 | − | − |

Based on Table 2, it is shown that a detection sensitivity in the example was 0.05 ng/mL, whereas a detection sensitivity of the comparative example was 0.25 ng/mL. This shows that the detection sensitivity in the example was increased about 5 times as compared with that of the comparative example.

(4) Evaluation 2: Evaluation of Specificity (4-1) Preparation of Test Sample

Human *Mycobacterium tuberculosis*, a *Mycobacterium tuberculosis* group, and a nontuberculous mycobacteria: group shown in Table 3 were cultured with BrothMIC (manufactured by Kyokuto Pharmaceutical Industrial Co., Ltd.) using a turbidimeter Vi-spec II (Kyokuto Pharmaceutical Industrial Co., Ltd.), and the culture was terminated when an optical density (OD: optical concentration) at a wavelength of 530 nm reached about 0.2. This cultured substance was used for a test sample.

TABLE 3

| | |
|---|---|
| Human *Mycobacterium tuberculosis* | *M. tuberculosis* H37Rv |
| | *M. tuberculosis* Aoyama-B |
| | *M. tuberculosis* linage 2 |
| *Mycobacterium tuberculosis* group | *M. bovis* |
| | *M. africanum* |
| | BCG Pasteur Strain |
| | BCG Connaught Strain |
| | BCG Tokyo Strain |
| | *M. microti* |
| Nontuberculous mycobacterial group | *M. avium* subsp. *Hominissuis* |
| | *M. intracellulare* |
| | *M. kansasii* |
| | *M. abscessus* subsp. *Abscessus* |
| | *M. abscessus* subsp. *Bolletii* |
| | *M. abscessus* subsp. *Massiliense* |
| | *M. chelonae* |
| | *M. fortuitum* |
| | *M. gordonae* |
| | *M. lentiflavum* |
| | *M. marinum* |
| | *M. scrofulaceum* |
| | *M. ulcerans* |
| | *M. xenopi* |
| | *M. malmoense* |

Measurement was performed in the same manner as (2-2) Measurement using comparative example, and (2-3) Measurement using example in "(2) Evaluation 1: evaluation of detection sensitivity". Regarding determination, whether a result was positive or negative was visually determined after completion of the reaction. In a case of visually observing the confirmation region having a line shape, a degree of coloration was discriminated as follows: "+" for coloration and "−" for no coloration.

(5) Result 2

Table 4 shows results of Evaluation 2.

TABLE 4

|  |  | Comparative Example | Example |
|---|---|---|---|
| Human Mycobacterium tuberculosis Mycobacterium tuberculosis group | M. tuberculosis H37Rv | + | + |
| | M. tuberculosis Aoyama-B | + | + |
| | M. tuberculosis linage 2 | + | + |
| | M. bovis | + | + |
| | M. africanum | + | + |
| | BCG Pasteur Strain | + | + |
| | BCG Connaught Strain | + | + |
| | BCG Tokyo Strain | + | + |
| | M. microti | + | + |
| Nontuberculous mycobacterial group | M. avium subsp. Hominissuis | + | + |
| | M. intracellulare | + | + |
| | M. kansasii | + | + |
| | M. abscessus subsp. Abscessus | + | − |
| | M. abscessus subsp. Bolletii | + | − |
| | M. abscessus subsp. Massiliense | + | − |
| | M. chelonae | + | − |
| | M. fortuitum | + | − |
| | M. gordonae | + | + |
| | M. lentiflavum | + | + |
| | M. marinum | + | + |
| | M. scrofulaceum | + | + |
| | M. ulcerans | + | + |
| | M. xenopi | + | + |
| | M. malmoense | + | + |

In diagnosis of tuberculosis, which is an infectious disease, by detecting lipoarabinomannan (LAM), regarding lack of specificity caused by cross-reactivity with a nontuberculous mycobacterial group, the lack being regarded as a problem in a case of performing a method using an existing kit in which a polyclonal antibody is used, cross-reactivity, with a nontuberculous mycobacterial group was ameliorated in Example in which a monoclonal antibody was used, which was a surprising result. Accordingly, the effect of improving specificity was clarified based on the results of Table 4.

Meanwhile, with respect to a polyclonal antibody that can bind to a plurality of epitopes, there was concern that diagnostic sensitivity would be insufficient due to a decrease in antigen detection sensitivity in a case of using a monoclonal antibody that binds to a single epitope. However, it was confirmed that, by performing a silver amplification reaction, lipoarabinomannan (LAM) could be detected with the same sensitivity as that of Comparative Example in which a polyclonal antibody was used, while still maintaining improvement in specificity for a nontuberculous mycobacterial group.

That is, in the present invention, it was possible to detect Mycobacterium tuberculosis with high-sensitivity and specificity by incorporating a compound containing silver, and a reducing agent capable of reducing silver ions, and by allowing at least one of a first antibody or a second antibody to be a monoclonal antibody, in an immunochromatographic kit for detecting Mycobacterium tuberculosis, the kit including a label substance modified with the first antibody against lipoarabinomannan, and a porous carrier having a reaction site holding the second antibody against lipoarabinomannan.

EXPLANATION OF REFERENCES

1: inspection strip
2: porous carrier
3: label-holding pad (glass fiber pad)
4: liquid-sending pad
6: absorption pad
7: back pressure-sensitive adhesion sheet
9: housing case
10: upper case
12: first protrusive deforming portion
14: second protrusive deforming portion
16: hole for dropwise addition of specimen liquid
18: observation window
20: lower case
21: porous carrier accommodation portion
22: absorption pad accommodation portion
24: second pot accommodation portion
30: middle member
32: first pot accommodation portion
34: tearing portion
35: flow path-forming portion
36: rear surface of flow path-forming portion 35
40: first pot for first amplification liquid
41: first amplification liquid
42: container
43: sheet member
45: second pot for second amplification liquid
46: second amplification liquid
47: container
48: sheet member
100: immunochromatographic kit
$L_1$: inspection region
$L_2$: confirmation region
$L_3$: amplification label region
D: gap (clearance)

Sequence List

International application 18F10206W1JP19034112_4. app based on the International Patent Cooperation Treaty

The invention claimed is:

1. A method of detecting a strain of *Mycobacterium* or a strain of BCG in a test specimen using a combination of antibodies consisting of a first antibody and a second antibody, the method comprising:

a step of spreading on a porous carrier a complex body of lipoarabinomannan in a test specimen and a label substance with which the first antibody is labelled, wherein the porous carrier has a reaction site having the second antibody immobilized therein, wherein the first antibody specifically binds to the lipoarabinomannan and the second antibody specifically binds to the 5-deoxy-5-methylthio-xylofuranose structure (MTX) of the lipoarabinomannan, wherein the first antibody is A194-01 monoclonal antibody and the second antibody is MoAb1 monoclonal antibody;

a step of trapping the complex body at the reaction site of the porous carrier; and a step of amplifying the label substance of the complex body trapped at the reaction site using a compound containing silver and a reducing agent that reduces silver ions, wherein the method detects a strain of *Mycobacterium tuberculosis, Mycobacterium bovis, Mycobacterium africanum, Mycobacterium microti*, BCG Pasteur strain, BCG Connaught strain, and BCG Tokyo strain in the test specimen and does not detect *Mycobacterium abscessus* subsp. *Abscessus, Mycobacterium abscessus* subsp. Bolletii, *Mycobacterium abscessus* subsp. Massiliense, *Mycobacterium* chelonae, and *Mycobacterium* fortuitum.

2. The method according to claim 1, the method further comprising detecting the label substance having an average particle size of equal to or more than 1 μm and equal to or less than 20 μm in the detection.

3. The method according to claim 1, wherein the label substance is a metal particle.

4. The method according to claim 1, wherein the label substance is gold, silver, platinum, or a compound thereof.

5. The method according to claim 1, wherein an average particle size of the label substance is 1 nm to 500 nm.

6. The method according to claim 1, wherein the compound containing silver is silver nitrate.

7. The method according to claim 1, wherein the reducing agent reducing the silver ions is $Fe^{2+}$.

8. The method according to claim 1, wherein the porous carrier is a nitrocellulose carrier.

9. The method according to claim 1, further comprising detecting the reducing agent that reduces the silver ions by using a coloring agent.

10. The method according to claim 9, wherein the coloring reagent is a compound that reacts with ions and develops color.

11. The method according to claim 9, wherein the coloring reagent is a compound that reacts with $Fe^{2+}$ ions and develops color.

12. The method according to claim 9, wherein the coloring reagent is a compound having a phenanthroline skeleton.

13. The method according to claim 9, wherein the coloring reagent is a compound that reacts with $H^+$ ions and develops color.

14. The method according to claim 9, wherein the coloring reagent is carried by the porous carrier.

* * * * *

SEQUENCE LISTING

```
Sequence total quantity: 18
SEQ ID NO: 1            moltype = AA  length = 6
FEATURE                 Location/Qualifiers
source                  1..6
                        mol_type = protein
                        organism = Homo sapiens
SEQUENCE: 1
RSIRSA                                                                  6

SEQ ID NO: 2            moltype =     length =
SEQUENCE: 2
000
```

```
SEQ ID NO: 3            moltype = AA   length = 9
FEATURE                 Location/Qualifiers
source                  1..9
                        mol_type = protein
                        organism = Homo sapiens
SEQUENCE: 3
QQYDFWYTF                                                                  9

SEQ ID NO: 4            moltype = AA   length = 8
FEATURE                 Location/Qualifiers
source                  1..8
                        mol_type = protein
                        organism = Homo sapiens
SEQUENCE: 4
GFNFEDFG                                                                   8

SEQ ID NO: 5            moltype = AA   length = 8
FEATURE                 Location/Qualifiers
source                  1..8
                        mol_type = protein
                        organism = Homo sapiens
SEQUENCE: 5
ISWNGANI                                                                   8

SEQ ID NO: 6            moltype = AA   length = 13
FEATURE                 Location/Qualifiers
source                  1..13
                        mol_type = protein
                        organism = Homo sapiens
SEQUENCE: 6
IDWYRDDYYK MDV                                                            13

SEQ ID NO: 7            moltype = DNA   length = 1356
FEATURE                 Location/Qualifiers
source                  1..1356
                        mol_type = other DNA
                        organism = Homo sapiens
SEQUENCE: 7
caagtgcagc tgttggagtc tgggggaggt gtggtacggc cggggggtc cctgagactc            60
tcctgtgcag cctctggatt caactttgaa gattttggca tgagctgggt ccgccaagct          120
ccagggaagg ggctggagtg gtctctagt attagttgga atggtgctaa ataggctat            180
gtagactctg tgaagggccg attcaccatc tccagagaca acgccaagaa ctccctatat          240
ctgcaaatga acagtctgag agccgaggac acggccttat attactgtgc gatagactgg          300
tacagagacg actactacaa gatggacgtc tggggcaaag gaccacggt caccgtctcc           360
tcagcctcga ccaagggccc atcggtcttc ccgctagcgc cctcctccaa gagcacctct          420
gggggcacag cggccctggg ctgcctggtc aaggactact ccccgaacc tgtgacggtc           480
tcgtggaact caggcgccct gaccagcggc gtgcacacct tcccggctgt cctacagtcc          540
tcaggactct actccctcag cagcgtggtg accgtgccct ccagcagctt gggcacccag          600
acctacatct gcaacgtgaa tcacaagccc agcaacacca aggtggacaa gaaagttgag          660
cccaaatctt gtgacaaaac tcacacatgc ccaccgtgcc cagcacctga actcctgggg          720
ggaccgtcag tcttcctctt ccccccaaaa cccaaggaca ccctcatgat ctcccggacc          780
cctgaggtca catgcgtggt ggtggacgtg agccacgaag accctgaggt caagttcaac          840
tggtacgtgg acggcgtgga ggtgcataat gccaagacaa agccgcggga ggagcagtac          900
aacagcacgt accgtgtggt cagcgtcctc accgtcctgc accaggactg gctgaatggc          960
aaggagtaca agtgcaaggt ctccaacaaa gccctcccag cccccatcga gaaaaccatc         1020
tccaaagcca aagggcagcc ccgagaacca caggtgtaca ccctgccccc atcccgggat         1080
gagctgacca agaaccaggt cagcctgacc tgcctggtca aaggcttcta tcccagcgac         1140
atcgccgtgg agtgggagag caatgggcag ccggagaaca actacaagac cacgcctccc         1200
gtgctggact ccgacggctc cttcttcctc tacagcaagc tcaccgtgga caagagcagg         1260
tggcagcagg ggaacgtctt ctcatgctcc gtgatgcatg aggctctgca caaccactac         1320
acgcagaaga gcctctccct gtctccgggt aaatga                                   1356

SEQ ID NO: 8            moltype = AA   length = 451
FEATURE                 Location/Qualifiers
source                  1..451
                        mol_type = protein
                        organism = Homo sapiens
SEQUENCE: 8
QVQLLESGGG VVRPGGSLRL SCAASGFNFE DFGMSWVRQA PGKGLEWVSS ISWNGANIGY           60
VDSVKGRFTI SRDNAKNSLY LQMNSLRAED TALYYCAIDW YRDDYYKMDV WGKGTTVTVS          120
SASTKGPSVF PLAPSSKSTS GGTAALGCLV KDYFPEPVTV SWNSGALTSG VHTFPAVLQS          180
SGLYSLSSVV TVPSSSLGTQ TYICNVNHKP SNTKVDKKVE PKSCDKTHTC PPCPAPELLG          240
GPSVFLFPPK PKDTLMISRT PEVTCVVVDV SHEDPEVKFN WYVDGVEVHN AKTKPREEQY          300
NSTYRVVSVL TVLHQDWLNG KEYKCKVSNK ALPAPIEKTI SKAKGQPREP QVYTLPPSRD          360
ELTKNQVSLT CLVKGFYPSD IAVEWESNGQ PENNYKTTPP VLDSDGSFFL YSKLTVDKSR          420
WQQGNVFSCS VMHEALHNHY TQKSLSLSPG K                                         451

SEQ ID NO: 9            moltype = DNA   length = 642
```

```
FEATURE                 Location/Qualifiers
source                  1..642
                        mol_type = other DNA
                        organism = Homo sapiens
SEQUENCE: 9
gaaatagtga tgacgcagtc tccagccacc ctgtctgtct ctccagggga aagagccacc   60
ctctcctgca gggccagtcg gagtattcgc agcgccttag cctggtacca gcacaaacct  120
ggccaggctc ccaggctcct catctttggt gcatccacca gggccactgg tatcccagcc  180
aggttcagtg gcagtgggtc tgggacagac ttcactctca ccgtcagcag catacggtct  240
gaggattctg cagtttatta ctgtcagcag tatgatttct ggtacacttt tggccagggg  300
accaagctgg agatcaaacg aactgtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtcgac aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgtt ag                     642

SEQ ID NO: 10           moltype = AA  length = 213
FEATURE                 Location/Qualifiers
source                  1..213
                        mol_type = protein
                        organism = Homo sapiens
SEQUENCE: 10
EIVMTQSPAT LSVSPGERAT LSCRASRSIR SALAWYQHKP GQAPRLLIFG ASTRATGIPA   60
RFSGSGSGTD FTLTVSSIRS EDSAVYYCQQ YDFWYTFGQG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 11           moltype = AA  length = 5
FEATURE                 Location/Qualifiers
source                  1..5
                        mol_type = protein
                        organism = Leporidae sp.
SEQUENCE: 11
TYYMT                                                                5

SEQ ID NO: 12           moltype = AA  length = 16
FEATURE                 Location/Qualifiers
source                  1..16
                        mol_type = protein
                        organism = Leporidae sp.
SEQUENCE: 12
TIDSYGNRYY ASWAKG                                                   16

SEQ ID NO: 13           moltype = AA  length = 10
FEATURE                 Location/Qualifiers
source                  1..10
                        mol_type = protein
                        organism = Leporidae sp.
SEQUENCE: 13
DDLGWNNDNI                                                          10

SEQ ID NO: 14           moltype = AA  length = 13
FEATURE                 Location/Qualifiers
source                  1..13
                        mol_type = protein
                        organism = Leporidae sp.
SEQUENCE: 14
QASESVYGNN QLA                                                      13

SEQ ID NO: 15           moltype = AA  length = 7
FEATURE                 Location/Qualifiers
source                  1..7
                        mol_type = protein
                        organism = Leporidae sp.
SEQUENCE: 15
KASTLAS                                                              7

SEQ ID NO: 16           moltype = AA  length = 13
FEATURE                 Location/Qualifiers
source                  1..13
                        mol_type = protein
                        organism = Leporidae sp.
SEQUENCE: 16
CGGYKGSTTD GAA                                                      13

SEQ ID NO: 17           moltype = AA  length = 119
FEATURE                 Location/Qualifiers
source                  1..119
```

-continued

```
                        mol_type = protein
                        organism = Leporidae sp.
SEQUENCE: 17
AQSVKESGGR LVTPGGSLTL TCTVSGIDLT TYYMTWIRQA PGKGLEWIGT IDSYGNRYYA  60
SWAKGQFTIS KTSSTTVDLK MTGLTASDTA TYFCTRDDLG WNNDNIWGPG TLVTVSSSS   119

SEQ ID NO: 18           moltype = AA  length = 112
FEATURE                 Location/Qualifiers
source                  1..112
                        mol_type = protein
                        organism = Leporidae sp.
SEQUENCE: 18
ELVMTQTPSS KSVPVGDTVT INCQASESVY GNNQLAWYQQ KPGQPPKLLI YKASTLASGV  60
PSRFKGSGYG TQFTLTISDV VCDDAATYYC GGYKGSTTDG AAFGGGTEVV VK          112
```